United States Patent [19]

Dorn

[11] 4,053,363

[45] Oct. 11, 1977

[54] SPUTUM ANALYSIS METHOD

[75] Inventor: Gordon L. Dorn, Dallas, Tex.

[73] Assignee: J. K. and Susie L. Wadley Research Institute and Blood Bank, Dallas, Tex.

[21] Appl. No.: 700,215

[22] Filed: June 28, 1976

[51] Int. Cl.² .................. C12K 1/00; G01N 33/16
[52] U.S. Cl. .................. 195/103.5 M; 195/103.5 R
[58] Field of Search .............. 195/103.5 R, 103.5 M; 23/230 B

[56] References Cited

U.S. PATENT DOCUMENTS 3,445,339 5/1969 Controni et al. .............. 195/103.5 M
3,883,425 5/1975 Dorn .............................. 210/31 C X Primary Examiner—David M. Naff
Attorney, Agent, or Firm—Richards, Harris & Medlock

[57] ABSTRACT

An in vitro diagnostic technique for quantitative analysis of human sputum, such as lung fluid, for the presence of microbial pathogens is provided wherein a sputum sample is contacted with a minor quantity of nontoxic saponin to degrade the viscosity of the sputum and thereafter the sputum is thoroughly admixed to distribute microbial pathogens generally uniformly therein. The sputum can be diluted as desired and then subjected to conventional analytical techniques, i.e., plating on growth media and recording results.

12 Claims, No Drawings

SPUTUM ANALYSIS METHOD

BACKGROUND OF THE INVENTION

This invention relates to the quantitative analysis of human sputums for the presence of microbial pathogens. In another aspect, this invention relates to a novel technique of liquefying sputum specimens with a saponin mucolytic agent.

The condition of pneumonia in a human patient generally comprises an acute inflammatory condition of a lung or lungs which can be caused by microbial pathogens such as bacteria or viruses as well as chemical irritants or foreign bodies. In order to determine the causal agent in a patient with a presumptive diagnosis of pneumonia, samples of lung fluid are required. The ideal specimens of lung fluid are homogeneous samples which can be obtained by surgical intervention, for example, transtrachael aspiration. As is typical, surgical intervention techniques are time consuming and present a risk to the patient. Fatal reactions have been reported resulting from transtrachael aspiration. For example, hypotoxic patients and those suffering from debilitating diseases such as blood dyscrasia are especially prone to serious complications from transtrachael aspiration.

As a consequence, most physicians rely on the early morning couph sputum specimen as the means of obtaining a lung fluid specimen. This technique is simple and very common. Unfortunately, the cough sputum specimen can be readily contaminated by the normal flora in the mouth, nose, posterior pharynx, and stomach. Furthermore, sputums from patients with pneumonia are very viscous and heterogeneous in nature and therefore difficult to disperse in a reproducible manner. Quantitative analysis of sputum cannot be accomplished on the very viscous heterogeneous sputums because it is generally necessary in quantitative analysis of specimens like sputum to dilute the specimen and thereafter plate minor portions of the specimen on various growth media and then determine the type and number of colonies of microbial organisms which result on the media. Generally, the maximum number of colonies which can be effectively counted on a petri dish is about 300. Furthermore, it has been accepted that normal sputum samples can contain contaminating microorganisms in quantites up to $10^5$ per milliliter, whereas, as causative organisms of pneumonia microorganisms are generally present in quantities greater than about $10^6$ per milliliter. Therefore, before a sputum specimen can be quantitatively analyzed, it must be diluted in a manner such that the microbial pathogens are uniformly dispersed in the resulting diluted sample. Accordingly, if a minor portion of this diluted sputum specimen is quantitatively analyzed for the type and number of microbial pathogens, the accurate number of microbial pathogens per milliliter of the sputum sample can be accurately calculated.

Thus, in order to reduce the problem of external contamination and heterogeneity of the sputum sample and provide a quantitative sputum analysis, several attempts have been made to digest the sputum specimen with enzymatic and chemical digestants. Several such digestants have been theretofore tried and all of the digestants have one or more of the following disadvantages: expensive; short shelf life; temperature sensitive; toxic to some or many pathogenic organisms; and require long digestion time. For example, a number of proteolytic enzymes have been tested in both purulent and mucoid sputum. Of such enzymatic materials, trypsin, elastase, and chymotrypsin appear the most effective, and enzymes such as bromelain, ficin or papain were only effective at extreme high concentrations, while plasmin has no detectable effect on sputum viscosity. All such proteolytic enzymes appear to be more effective with mucoid sputums than with purulent sputums. The most widely used digestants for quantitative sputum analysis are aqueous solutions of N-acetylcysteine and Cleland's reagent (1,4-dithio-mesoerithritol). In general, Cleland's reagent exhibits greater mucolytic activity than N-acetylcysteine at lower concentrations, but Cleland's reagent generally loses its mucolytic activity in relatively short periods of time in aqueous solution. Furthermore, both of these reagents are somewhat toxic to microbial pathogens at concentrations needed for rapid digestion of sputum.

Consequently most sputum specimens are processed by a nonquantitative streaking technique, which generally involves streaking the heterogeneous sputum specimen on various growth media. These techniques lead to a substantial number of false positive cultures, and in many instances, overgrowth of the pathogenic organisms by contaminating microorganisms.

SHORT STATEMENT OF THE INVENTION

According to the invention, I have discovered that certain purified saponins exhibit mucolytic activity and will effectively degrade sputum samples including both purulent and mucoid sputums and uniformly disperse microbial pathogens therewithin without harming the pathogens.

According to one embodiment of the subject invention, a novel technique for the quantitative analysis of sputums is provided which includes the steps of contacting the sputum specimen after it is collected with an effective mucolytic portion of a nontoxic saponin to convert the sputum specimen to a substantially uniform viscosity and mixing the specimen such that any pathogens are uniformly distributed therewithin and thereafter conducting quantitative analysis techniques on the resulting specimen.

DETAILED DESCRIPTION OF THE INVENTION

The nontoxic saponin which is utilizable within the scope of the subject invention can be purified by the method disclosed in U.S. Pat. No. 3,883,425 which patent is herein incorporated by reference into this specification.

Saponins are glycosides widely distributed in plants and are capable of forming oil-in-water emulsions, and act as protective colloids. Each saponin molecule consists of a sapogenin which constitutes the aglucone moiety of the molecule, and a sugar.

The sapogenin is either a triterpenoid (usually a pentacyclic structure, such as quillaic acid), or a stearoid structure (usually having a spiro acetal side chain as in diosgenin). The sugar portion of the saponin glucoside includes one or more sugars such as glucose, sucrose, xylose, a pentose or methyl pentose, or other sugars. On hydrolysis, the saponins yield the sapogenin and one or more of these sugars.

Commercially available saponins comprise a white to brown amorphous powder which is pungent, and has a disagreeable taste and odor. This powder is very soluble in water and foams very strongly when shaken with water.

Commercial saponins are prepared by extracting plant tissue with water and/or other organic solvents, such as alcohol and recovering saponin by precipitation, recrystallization and the like. Saponins are widely distributed in plants. For example, saponins are very widely distributed in the plant family caryophyllaceae. Specific examples of saponin sources include soap bark, panama wood, soap berry, liquorice, and the like. A specific example of a process for producing commercial saponin is described in Kingzette's Chemical Encyclopedia, D. H. Hey, 9th Edition, (1966) which includes either extracting powdered soap bark (Quillaria saponaria) with hot alcohol or by boiling powdered dry aqueous extract of such bark with alcohol, and allowing saponin to crystallize from the alcohol upon cooling.

Saponins are practically nontoxic to humans upon oral ingestion, but act as powerful hemolytics when injected into the bloodstream, thereby dissolving the red blood corpuscles. Because of this characteristic, saponins have been conventionally used in hemotology laboratories for lysing the red cells whenever their presence interferred with other procedures, e.g., hemoglobin determinations and white cell counts.

As set forth in said patent, U.S. Pat. No. 3,883,425, a technique is provided for removing microbial toxins from saponin which is extracted from a plant source by removing consitutents from an aqueous solution of said saponin which have an apparent molecular weight of less than about 600, e.g., a molecular size in aqueous solution between about 140 to about 600. One technique disclosed in said patent is to form an aqueous solution of a commercial saponin extract from plants and thereafter pass the solution through a microporous filter membrane which has a mean actual pore size no smaller than about 11 angstroms in diameter and no larger than about 24 angstroms in diameter. The aqueous solution which passes through the microporous filter membrane will contain the antimicrobial toxin, and the filter will exclude the saponin material.

I have now found that such purified saponin plant extracts are effective mucolytic agents in that they will efficiently degrade all types of sputum and disperse microbial pathogens therewithin without harming the pathogens.

In carrying out the method of the subject invention, the sputum sample is collected by any conventional technique. Thereafter the sputum is admixed with a minor but effective mucolytic amount of the nontoxic saponin described above. Preferably the saponin is in aqueous solution when admixed with the sputum. The aqueous solution can be of any convenient concentration such that when the desired amount of solution is admixed with the sputum specimen, sufficient saponin will be present to degrade the same. Generally, it is necessary from about 0.1% by weight to about 20% by weight and preferably from about 1.0% by weight to about 10% by weight and even more preferably from about 5% by weight to about 10% by weight of saponin be contained in the resultant mixture of saponin and sputum.

In addition, it is preferable to add to the resultant mixture of saponin and sputum from about 0.1% by weight to about 20% by weight and more preferably from about 5% by weight to about 10% by weight of an antifoamant which is nondeleterious to microbial pathogens. Suitable such antifoam agents include materials sold under the trademarks of Dow X Antifoam B and Dow X H 10. These agents contain chemical polymers of dimethylsiloxane and a sterilizable, e.g., autoclavable, nonionic emulsifier such as the type sold under the trademark of Triton X. The material sold under the trademark of Dow X H 10 may be preferred since it is very stable to sterilization by autoclaving. The saponin effectively degrades all types of sputum both mucoid and purulent very rapidly to form a mixture of uniform viscosity.

The sputum sample is then thoroughly admixed to uniformly disperse the microorganisms therewithin. If desired, portions of the resulting degraded sputum sample can be plated directly on various media to obtain an improved qualitative sputum analysis which is not subject to the substantial number of false-positive cultures and overgrowth of pathogenic flora by contaminating microorganisms as is the conventional qualitative technique which does not utilize degraded sputum.

When conducting an improved quantitative analysis of sputum in accordance with the subject invention, the saponin treated sputum is diluted as desired, e.g., 1:100–1:1000 with phosphate buffered normal saline, pH 7.2 or any other suitable diluent which will not interfere in the analysis technique and is nontoxic to the microbial pathogens. The resulting diluted specimen is thoroughly admixed to assure uniform distribution of the microbial pathogens throughout the solution. Next, samples of the diluted solution are added to conventional growth media and allowed to incubate. Next, any resulting colonies on the media can be identified and counted and by knowing the extent of dilution of the sputum specimen, the total quantity of different types of microbial pathogens can thereby be easily calculated. Alternately, if desired, the nondiluted specimen can be subjected to microscopic examination.

The following examples are presented to more specifically illustrate the subject invention.

EXAMPLE I

In this Example, the toxicity of various known mucolytic agents was compared to that of saponin. In each instance, the strains of bacteria shown in Table 1 below were grown overnight in the growth media indicated in Table 1 and the turbidity of the resultant growth media was adjusted with sterile saline to a barium sulfate standard to approximately $10^8$ bacteria per milliliter. Thereafter the resulting broth was diluted 1:200 in nutrient broth. Next, a 40 weight percent solution of saponin which was purified in accordance with the procedure set forth in U.S. Pat. No. 3,883,425 (to thereby remove toxic contaminants therefrom which have an apparent molecular weight of less than about 600 in aqueous solution) was added to the type of growth broth for the particular bacteria as indicated in Table 1. Thereafter, 1 milliliter of each bacterial-growth broth suspension was added to 1 milliliter of saponin solution described above to give a final concentration of 20% by weight saponin, and then was incubated overnight at 37° C. A control and test suspension was also streaked on rich agar containing 1 weight percent glucose, or blood agar.

The other compounds tested for toxicity were Cleland's reagent (1,4-dithio-mesoerithritol), N-acetylcysteine, and sodium lauryl sulfate. These mucolytic agents were prepared in the concentrations and in the growth broth for each of the microorganisms as indicated in Table 1 and tested for toxicity in the same manner as the saponin described above.

If the particular bacteria grew in the broth containing the indicated quantity of mucolytic agent, the run was repeated to see if growth could be duplicated in a second run. If growth was no obtained either the first or second time, a third run was made in an attempt to grow the bacteria. In some instances, a third run was made even though bacteria grew in the prior two runs. Therefore, in the table a plus indicates a successful growth run and a minus indicates a negative growth run. More specifically:

+ + + = grew three out of three times
− − − = did not grow once out of three times
− − + = grew one out of three times
− + + = grew twice out of three times The results are set forth in Table 1 below:

Grade 4: purulent - yellow or greenish, cloudy, polymorphonuclear cells more than 70%, and greater than ½ of the field covered with cells.

In each instance, the cellular density was determined by observing what percentage of a 40X field is filled with cells on a wet mount sample. The cytology is determined by staining (Papanicolaou) a slide, counting 200 cells of the sample and identifying the polymorphonuclear cells (PMN), eosinophils, basophils, macrophages, monocytes, and lymphocytes.

After each sputum sample was graded, a routine analysis was run thereof which includes making 6 semi quantitative streaks with part of the sputum sample on a Table 1

| Organism | Type of Growth Broth* | Mucolytic Agent and Percent Concentration | | | | | | |
|---|---|---|---|---|---|---|---|---|
| | | Saponin 20% | Cleland's 0.1% | Cleland's 0.5% | N-acetylcysteine 0.5% | N-acetylcysteine 5.0% | Sodium lauryl sulfate 2.5% | Sodium lauryl sulfate 10.0% |
| Escherichia coli I | 1 | + + | + + + | − + + | + − + | − − − | + + + | + + + |
| Staphylococcus XIII 1 | | + + + | − − − | + + − | − − − | − − − | − − − | − − − |
| Pseudomonas species | 1 | + + | + + + | − − − | + + − | − − − | + − + | + − + |
| Candida species | 1 | + + | + + + | − + + | + + + | − − − | + − − | − − − |
| Torulopsis glabrata | 1 | + + | + + + | − + − | + + + | − − − | − − − | − − − |
| Streptococcus pyogenes | 2 | + + | + + | − − | + − | + − | − − | − − |
| Streptococcus pneumoniae | 3 | + + | + + | − − | − − | − − | − − | − − |
| Citrobacter freundii | 1 | + + | + + + | + + + | − + + | − − − | + + + | + + + |
| Klebsiella pneumoniae | 1 | + + | + + + | − + + | + + + | − − − | + + + | + + + |
| Enterobacter aerogenes | 1 | + + | + + + | − + + | + + + | − − − | + + + | + + + |
| Salmonella cholerasuis | 1 | + + | + + + | − + + | − − + | − − − | + + + | + + + |
| Proteus mirabilis | 1 | + + | + + + | − + + | + + + | − − − | + + + | + + + |
| Listeria monocytogenes | 4 | + + | + + + | + + − | + − − | − − − | − − − | − − − |
| Neisseria meningitidis | 4 | + + | − | − | − | − | − | − |
| Brucella suis | 4 | + + | − + | − − | + − | − − | − − | − − |
| Bacteroides fragilis | 5 | + + | + + | + − | + − | − − | − − | − − |
| Clostridium perfringins | 5 | + + | + + | + − | + − | − | − | − |
| Propionibacterium shermanii | 5 | + + | + − | + − | − − | − − | − − | − − |
| Mycoplasma hominis | 6 | + + | NT | NT | NT | NT | NT | NT |

*1 grew in rich broth containing 1 wt % glucose.
2 grew in Todd - Hewett broth and thereafter streaked on blood.
3 grew in rich broth containing 1 wt % glucose and thereafter streaked on blood.
4 grew in rich broth containing 1 wt % glucose and thereafter streaked on blood in a CO₂ jar.
5 grew in a peptone yeast glucose maltose broth and thereafter streaked on blood in an anaerobic jar.
6 originally grew in a PPLO broth and thereafter streaked on PPLO agar in a CO₂ jar.
NT not tested.

As can be seen from Table 1 above, the relatively high concentration of the purified saponin did not kill or inhibit the growth of any of the micoorganisms tested. However, each of the other mucolytic agents tested prevented growth of several of the microorganisms at much lower concentration than the saponin. It should also be noted that even at recommended use concentration of presently used mucolytic agents (0.5% N-acetylcysteine and 0.1% Cleland's reagent) toxicity against several organisms was noted.

EXAMPLE II

Clinical analyses of several sputum samples was conducted after the samples had been dissolved in nontoxic saponin and the results compared to the routine sputum analysis that is conventionally conducted in a typical hospital. Initially, an early morning sputum specimen was collected and a wet prep and smear were made to grade the sputum and to observe characteristics thereof such as spores. The sputums were graded 1 through 4 according to the following protocol:

Grade 1: saliva -frothy, clear, colorless, mostly epithelial cells on a 40X field.
Grade 2: mucoid -colorless, clear to translucent, majority of eosinophils and macrophages, polymorphonuclear cells less than 60%, and less than ½ of a 40X field having cells.
Grade 3: mucopurulent - colorless to greenish, slightly translucent, and approximately ½ of the field filled with cells.

blood agar plate (BA); on a chocolate agar plate (CHOC); on a eosin methylene blue plate (EMB); on a mannitol salts plate (MAN); on a mannitol salts containing penicillin plate (MAN-PEN); and on a Sabourand's + gentamicin plate (SDA-GENT), and allowing any bacteria to grow on the plate and thereafter identifying the same. The remaining part of each specimen was thereafter digested with an equal amount of 10 weight percent saponin (which has been purified in accordance with U.S. Pat. No. 3,833,425) and 0.1 m sodium citrate, and an antifoaming agent (Antifoam B Emulsion - Dow Corning) to give a final concentration of 5% by weight saponin therein. Thereafter the saponin-sputum mixture is vortexed for at least 30 seconds.

Next, the original digested sputum was streaked onto the following plates: BA; CHOC; EMB; MAN; MAN-PEN; and SDA-GENT. Thereafter, two 1:100 dilutions were made from a portion of the digested sputum into saline bottles to give $10^2$ and $10^4$ dilutions, e.g., 0.1 milliliters sputum was placed into a 9.9 milliliters saline for the $10^2$ dilution, and 0.1 milliliters from the $10^2$ dilution was placed into 9.9 milliliters of saline to make the $10^4$ dilution. Next, a 0.01 milliliter loop was used to streak from the $10^4$ dilution bottle on to the following plates: BA; CHOC; EMB; MAN; MAN+PEN; and SDA+λ GENT, to give a final definite dilution of $10^6$. Thereafter, another 0.01 milliliter sample was streaked onto SDA gentamicin from the $10^2$ dilution bottle to give a definite dilution of $10^4$. All the plates were incubated and read in 24 and 48 hours. The SDA plates were also read after one week. The plates were interpreted as follows:

a. an interpretation of normal flora (normal level and type of microorganisms found in nasopharyngeal passages) for Alpha streptococcus and Neissera and diphtheroids occurring in the $10^6$ and $10^7$ range.

b. positive infection for all other nonyeast organisms (other than set forth in (a) above) occurring in the $10^6$ and greater range.

c. $10^5$ was interpreted as 1-5 organisms found randomly on a set of plates as a possible positive.

d. $10^3$ and upon which is 1 and 5 organisms found randomly on a set of plates is a possible positive for *Candida Albicans*, and a positive for all other yeasts.

The results are set forth in Table 2 below.

Table 2

CLINICAL RESULTS OF SPUTUM ANALYSIS BY ROUTINE AND QUANTITATIVE ANALYSIS

| Case No. | Grade Sputum | Routine Analysis | Conclusion | Quantitative Analysis | Conclusion |
|---|---|---|---|---|---|
| 1 | 2 | Light *Enterococcus*, light *Klebsiella pneumoniae*, light *Staphylococcus epidermidis*, light *Pseudomonas* | Normal Flora | Normal Flora | Normal Flora |
| 2 | 4 | Light *Staphylococcus aureus* | Normal Flora | $2 \times 10^7$ *Neisseria perflava* | Possible positive for *Neisseria perflava* |
| 3 | 1 | Moderate *Serratia marcescens*, light *Pseudomonas* | Significant growth *Serratia marcescens* | $1 \times 10^6$ *Pseudomonas aeruginosa*, $1 \times 10^5$ *Serratia marcescens* | Positive for *Pseudomonas aeruginosa*, possible positive for *Serratia marcescens* |
| 4 | 2 | Normal Flora | Normal Flora | Normal Flora | Normal Flora |
| 5 | 2 | Normal Flora | Normal Flora | Normal Flora | Normal Flora |
| 6 | 2 | Normal Flora | Normal Flora | Normal Flora | Normal Flora |
| 7 | 1 | Light *Pseudomonas*, light *Candida albicans* | Normal Flora | $1 \times 10^5$ *Pseudomonas aeruginosa* | Possible positive for *Pseudomonas aeruginosa* |
| 8 | 4 | Heavy *Klebsiella pneumonia*, light *Candida tropicalis*, light *Enterococcus* | Positive for *Klebsiella pneumoniae* | $2.5 \times 10^5$ yeast (*Candida krusei* and *Torulopsis glabrata*), $1 \times 10^8$ *Klebsiella pneumonia*, $4 \times 10^7$ *Enterococcus* | Positive for yeast, *Klebsiella pneumoniae* and *Enterococcus* (D) |
| 9 | 4 | Moderate *Candida albicans* | Positive for *Candida albicans* | TNTC *Hansenula polymorpha*, $1 \times 10^5$ *Klebsiella pneumoniae* | Positive for yeast, possible positive for *Klebsiella pneumoniae* |
| 10 | 1 | Normal Flora | Normal Flora | $1 \times 10^5$ *Staphylococcus aureus* | Normal Flora |
| 11 | 3 | Moderate *Klebsiella pneumoniae*, light *Candida albicans* | Positive for *Klebsiella pneumoniae* | $1 \times 10^6$ *Klebsiella pneumoniae*, $1 \times 10^5$ *Candida albicans* | Positive for *Candida albicans*, possible positive for *Klebsiella pneumoniae* |
| 12 | 1 | Light *Pseudomonas fluorescens*, light *Candida albicans* | Normal Flora | $1 \times 10^6$ *Candida albicans*, $1 \times 10^6$ *Pseudonomas fluorescens*, $1 \times 10^5$ *Klebsiella pneumoniae* | Positive for *Candida albicans* and *Pseudomonas fluorescens*, possible positive for *Klebsiella pneumoniae* |
| 13 | 2 | Normal Flora | Normal Flora | Normal Flora | Normal Flora |
| 14 | 3 | Moderate *Klebsiella pneumoniae*, light *Candida albicans* | Positive for *Klebsiella pneumoniae* | $1 \times 10^6$ *Candida albicans* | Positive for *Candida albicans* |
| 15 | 2 | Light *Staphylococcus aureus*, light *Candida albicans* | Normal Flora | $1 \times 10^6$ *Candida albicans*, $1 \times 10^6$ *Staphylococcus aureus* | Positive for *Candida albicans* and *Staphylococcus aureus* |
| 16 | 2 | *Candida albicans* | Positive for *Candida albicans* | $1 \times 10^3$ *Candida albicans* | Possible positive for *Candida albicans* |
| 17 | 2 | Light Beta streptococcus, light *Staphylococcus aureus*, light *Candida albicans* and *Candida tropicalis* | | $2 \times 10^5$ *Torulopsis magii*, $4 \times 10^5$ *Candida albicans* | Positive for *Torulopsis magii* and *Candida albicans* |
| 18 | 4 | *Haemophilus influenzae* | Positive for *Haemophilus influenzae* | $6 \times 10^8$ *Haemophilus influenzae*, $1 \times 10^3$ *Torulopsis glabrata* | Positive for *Haemophilus influenzae*, possible positive for *Torulopsis glabrata* |
| 19 | 1 | Normal Flora | Normal Flora | Normal Flora | Normal Flora |
| 20 | 3 | Heavy *Enterobacter cloacae*, heavy *Klebsiella pneumoniae*, heavy *Staphylococcus epidermidis* | Positive for *Enterobacter cloacae*, *Klebsiella pneumoniae* and *Staphylococcus epidermidis* | $>10^8$ *Klebsiella pneumoniae*, $>10^8$ *Enterobacter cloacae*, $10^5$ *Candida krusei*, $10^5$ *Torulopsis glabrata*, $10^4$ *Candida tropicalis* | Positive for *Klebsiella pneumoniae*, *Enterobacter cloacae*, *Candida krusei*, *Torulopsis glabrata* and *Candida tropicalis* |
| 21 | 3 | Normal Flora | Normal Flora | 1 *Penicillium humulii* | Normal Flora |
| 22 | 2 | Normal Flora | Normal Flora | Normal Flora | Normal Flora |
| 23 | 2 | Normal Flora | Normal Flora | Normal Flora | Normal Flora |
| 24 | 2 | Light *Candida tropicalis* | Normal Flora | $2.5 \times 10^4$ *Candida tropicalis*, $1.5 \times 10^4$ *Torulopsis* | Positive for *Candida tropicalis* and *Torulopsis glabrata* |

Table 2-continued
CLINICAL RESULTS OF SPUTUM ANALYSIS BY ROUTINE AND QUANTITATIVE ANALYSIS

| Case No. | Grade Sputum | Routine Analysis | Conclusion | Quantitative Analysis | Conclusion |
|---|---|---|---|---|---|
| 25 | 4 | Light *Klebsiella pneumoniae*, 3 col. *Staphylococcus aureus* | Normal Flora | glabrata ~$10^5$ *Klebsiella pneumoniae* | Possible positive for *Klebsiella pneumoniae* |
| 26 | 3 | Normal Flora | Normal Flora | Normal Flora | Normal Flora |
| 27 | 4 | Light *Candida tropicalis* | Normal Flora | $10^6$ *Escherichia coli*, $10^3$ *Torulopsis glabrata* | Possible positive for *Escherichia coli* and *Torulopsis glabrata* |
| 28 | 4 | Normal Flora | Normal Flora | $6 \times 10^7$ *Haemophilus*, $1 \times 10^3$ *Torulopsis glabrata* | Possible positive for *Haemophilus* and *Torulopsis glabrata* |
| 29 | 2 | Normal Flora | Normal Flora | Normal Flora | Normal Flora |
| 30 | 3 | Moderate *Acinetobacter calcoaceticus* (H) | Positive for *Acinetobacter calcoaceticus* (H) | $2 \times 10^8$ *Acinetobacter calcoaceticus* (H), $1 \times 10^8$ *Haemophilus* $1 \times 10^8$ *Haemophilus* | Positive for *Acinetobacter calcoaceticus* and *Haemophilus* and *Haemophilus* |
| 31 | 4 | Normal Flora | Normal Flora | $1 \times 10^8$ *Diplococcus* | Positive for *Diplococcus* |
| 32 | 3 | Normal Flora | Normal Flora | Normal Flora | Normal Flora |
| 33 | 2 | *Candida albicans* | Positive for *Candida albicans* | $1 \times 10^5$ *Candida albicans* | Positive for *Candida albicans* |
| 34 | 2 | Normal Flora | Normal Flora | Normal Flora | Normal Flora |
| 35 | 3 | Light *Enterobacter cloacae* | Normal Flora | $10^6$ *Pseudomonas aeruginosa*, $10^5$ *Proteus mirabilis* | Possible positive for *Pseudomonas aeruginosa* and *Proteus mirabilis* |
| 36 | 3 | Light *Proteus vulgaris* | Normal Flora | $1 \times 10^6$ *Proteus vulgaris* | Possible positive for *Proteus vulgaris* |
| 37 | 3 | Light *Candida albicans* | Normal Flora | Normal Flora | Normal Flora |
| 38 | 2 | Normal Flora | Normal Flora | $1 \times 10^3$ *Candida albicans* | Possible positive for *Candida albicans* |
| 39 | 3 | Moderate *Klebsiella pneumoniae*, light *Enterococcus* and *Candida tropicalis* | Positive for *Klebsiella albi-* | $10^5$ *Klebsiella pneumoniae*, $10^5$ *Enterococcus* $10^5$ *Candida albicans* | Positive for *Candida albicans*, possible positive for *Enterococcus* and *Klebsiella pneumoniae* |
| 40 | 3 | Heavy *Candida albicans*, light *Klebsiella pneumonidae* | Positive for *Canadida albicans* | $10^9$ *aeruginosa, Klebsiella pneumoniae*, $>10^5$ *Candida albicans* | Positive for *Klebsiella pneumoniae Candida albicans* |
| 41 | 4 | | | $10^6$ *Haemophilus* | Possible positive for *Haemophilus* |
| 42 | 2 | Normal Flora | Normal Flora | Normal Flora | Normal Flora |
| 43 | 4 | Light *Candida albicans* | Normal Flora | $10^5$ *Candida albicans* | Positive for *Candida albicans* |
| 44 | 4 | heavy *Candida albicans* ratia liquefa- | Positive for *Candida albicans* ble positive for | $>10^6$ *Candida albicans*, $10^5$ *Serratia possi- ciens*, $10^5$ *Pseudomonas* | Positive for *Candida albicans, liquefaciens Serratia liquefaciens* and *Pseudomonas* |
| 45 | 2 | Normal Flora | Normal Flora | Normal Flora | Normal Flora |
| 46 | 4 | *Proteus mirabilis* and gram positive cocci (unable to isolate) | Positive for *Proteus mirabilis* | $10^6$ *Proteus mirabilis* | Possible positive for *Proteus mirabilis* |
| 47 | 4 | Light *Klebsiella pneumoniae* | Normal Flora | $10^7$ *Klebsiella pneumoniae*, *Basidiomycetes* | Positive for *Klebsiella pneumoniae* |
| 48 | 3 | *Staphylococcus aureus* | | Normal Flora | Normal Flora |
| 49 | 4 | Heavy *Klebsiella pneumoniae* | Positive for *Klebsiella pneumoniae* | $1 \times 10^8$ *Klebsiella pneumoniae* | Positive for *Klebsiella pneumoniae* |
| 50 | 2 | Normal Flora | Normal Flora | Normal Flora | Normal Flora |
| 51 | 3 | Light *Klebsiella pneumoniae*, light Beta Streptococcus, moderate *Citrobacter freundii* | Positive for *Citrobacter freundii* | $1 \times 10^6$ *Pseudomonas putida* | Possible positive for *Pseudomonas putida* |
| 52 | 3 | Normal Flora | Normal Flora | Normal Flora | Normal Flora |
| 53 | 4 | Moderate *Candida albicans* | Positive for *Candida albicans* | $2 \times 10^5$ *Candida albicans* and *Candida tropicalis* | Positive for *Candida albicans* and *Candida tropicalis* |
| 54 | 3 | Light *Candida albicans* | Normal Flora | $1 \times 10^3$ *Candida albicans* | Possible positive for *Candida albicans* |
| 55 | 2 | Heavy *Klebsiella pneumoniae*, light *Escherichia coli* | Positive for *Klebsiella pneumoniae* | $1 \times 10^8$ *Neisseria* species, 1 *Fusarium* species | Possible positive for *Neisseria* species |
| 56 | 3 | Light *Klebsiella pneumoniae*, light *Candida tropicalis* | Normal Flora | ~$3 \times 10^5$ *Candida para-psilosis* | Positive for *Candida para-psilosis* |
| 57 | 3 | Light *Haemophilus*, light *Candida albicans* | Normal Flora | $1 \times 10^3$ *Candida albicans*, $1 \times 10^8$ *Haemophilus* | Positive for *Haemophilus* possible positive for *Candida albicans* |

Table 2-continued
CLINICAL RESULTS OF SPUTUM ANALYSIS BY
ROUTINE AND QUANTITATIVE ANALYSIS

| Case No. | Grade Sputum | Routine Analysis | Conclusion | Quantitative Analysis | Conclusion |
|---|---|---|---|---|---|
| 58 | 4 | Moderate *Haemophilus* | Positive for *Haemophilus* | $1.0 \times 10^8$ *Haemophilus* | Positive for *Haemophilus* |
| 59 | 2 | Heavy *Klebsiella pneumoniae*, light *Escherichia coli* | Positive for *Klebsiella pneumoniae* | $1 \times 10^6$ *Klebsiella pneumoniae* | Possible positive for *Klebsiella pneumoniae* |
| 60 | 4 | Light *Haemophilus* | Normal Flora | $>3 \times 10^8$ *Haemophilus* | Positive for *Haemorphilus* |
| 61 | 2 | Light *Klebsiella pneumoniae* | Normal Flora | $1 \times 10^6$ *Klebsiella pneumoniae*, $1 \times 10^3$ *Candida albicans* | Positive for *Klebsiella pneumoniae*, possible positive for *Candida albicans* |
| 62 | 4 | Normal Flora | Normal Flora | Normal Flora | Normal Flora |
| 63 | 4 | *Haemophilus* | Positive for *Haemophilus* | $1 \times 10^7$ *Haemophilus* | Positive for *Haemophilus* |
| 64 | 2 | Light *Serratia liquefaciens* | Normal Flora | Normal Flora | Normal Flora |
| 65 | 4 | Normal Flora | Normal Flora | Normal Flora | Normal Flora |
| 66 | 3 | Normal Flora | Normal Flora | Normal Flora | Normal Flora |
| 67 | 3 | Heavy *Klebsiella pneumoniae*, light *Enterococcus* | Positive for *Klebsiella pneumoniae* | $1 \times 10^7$ *Enterococcus* (D), $3 \times 10^8$ *Klebsiella pneumoniae* | Positive for *Enterococcus* (D) and *Klebsiella pneumoniae* |
| 68 | 2 | Normal Flora | Normal Flora | Normal Flora | Normal Flora |
| 69 | 2 | Moderate *Staphylococcus aureus*, light Alpha streptococcus | Positive for *Staphylococcus aureus* | $1 \times 10^7$ *Staphylococcus aureus* | Positive for *Staphylococcus aureus* |
| 70 | 2 | Heavy *Serratia liquefaciens*, light Alpha Streptococcus | Positive for *Serratia liquefaciens* | $>10^8$ *Serratia liquefaciens* | Positive for *Serratia liquefaciens* |
| 71 | 2 | Normal Flora | Normal Flora | Normal Flora | Normal Flora |
| 72 | 3 | Moderate *Enterobacter aerogenes* | Positive for *Enterobacter aerogenes* | $1 \times 10^7$ *Enterobacter aerogenes*, $1 \times 10^6$ *Serratia liquefaciens* | Positive for *Enterobacter aerogenes*, possible positive for *Serratia liquefaciens* |
| 73 | 2 | Normal Flora | Normal Flora | $1 \times 10^7$ *Serratia liquefaciens* | Positive for *Serratia liquefaciens* |
| 74 | 4 | Light *Klebsiella pneumoniae*, light *Enterococci* | Normal Flora | Normal Flora | Normal Flora |
| 75 | 2 | *Enterobacter, Candida albicans* | | $1 \times 10^4$ *Candida albicans* | Positive for *Candida albicans* |
| 76 | 4 | *Enterobacter aerogenes, Candida albicans* | | $>1 \times 10^8$ *Enterobacter cloacae*, $1.5 \times 10^5$ *Candida albicans* | Positive for *Enterobacter cloacae* and *Candida albicans* |
| 77 | 4 | Light *Klebsiella pneumoniae* (2) | Normal Flora | $>1 \times 10^8$ *Haemophilus*, $1 \times 10^6$ *Klebsiella pneumoniae* and *Hormodendrum* species, $1 \times 10^6$ *Pasteurella* | Positive for *Haemophilus*, possible positive for *Klebsiella pneumoniae* and *Pasteurella* |
| 78 | 3 | Normal Flora | Normal Flora | Normal Flora | Normal Flora |
| 79 | 2 | Normal Flora | Normal Flora | Normal Flora | Normal Flora |
| 80 | 3 | Alpha streptococcus, *Neisseria* | Normal Flora | $1 \times 10^8$ *Haemophilus*, $1 \times 10^7$ *Klebsiella pneumoniae* | Positive for *Haemophilus* and *Klebsiella pneumoniae* |

As can be seen in Table 2, the routine clinical method and the quantitative method (which utilized the saponin digestion step) were carried out on 80 sputum specimens, and 29 results differed. In 26 cases, the quantitative method found a positive when the routine clinical lab method did not, and in 3 cases, the routine clinical lab method found a positive whose numbers were not high enough to be considered a positive by quantitative standards. It is particularly noted that in 7 patients *Haemophilus influenzae* was found in the quantitative method on chocolate plates greater than $10^7$ per milliliter and was not detected by the routine clinical lab because of overgrowth. This particular organism has great clinical significance in pneumonia. Also, on four occasions, other organisms which constituted double infections were overgrown and not detected by the routine clinical laboratory analysis. Most of the differences in the results set forth in the table were in yeasts shown as positive by the quantitative method, and either not detected or considered light grown by the routine clinical laboratory method.

Next, to correlate laboratory findings with patient history, Table 3 shows a few correlations from the throat and lung autopsies. The results of these correlations is set forth in Table 3 below:

Table 3

| Patient No. | Culture | Results |
|---|---|---|
| I | Throat | Light *Candida albicans* |
| | Sputum* | $1 \times 10^5$ *Candida albicans*, $1 \times 10^5$ *Proteus* and *Pseudomomas aeruginosa* |
| II | Throat | Normal Flora |
| | Sputum | $10^8$ *Haemophilus*, $10^6$ *Klebsiella pneumoniae*, $10^6$ *Pasturella* |
| III | Sputum | $1 \times 10^9$ *Klebsiella pneumoniae* |
| | Throat | Moderate *Candida albicans* |
| IV | Throat | Light *Pseudomonas aeruginosa* |
| | Sputum | $1 \times 10^5$ *Pseudomonas aeruginosa* |
| V | Throat | *Staphylococcus, Streptococcus* Beta, light *Klebsiella pneumoniae* |
| | Sputum | $10^5$ *Klebsiella pneumoniae* |
| | Lung autopsy | Heavy *Klebsiella pneumoniae* |
| VI | Throat | Light *Candida albicans* |
| | Sputum | $>10^6$ *Candida albicans*, $10^5$ *Serratia Liquefaciens*, $10^5$ *Pseudomonas* |
| VII | Throat | *Enterococcus, Escherichia coli* |
| | Sputum | Normal Flora |

Table 3-continued

| Patient No. | Culture | Results |
|---|---|---|
| VIII | Sputum | Normal Flora |
| | Lung autopsy | *Enterbacter aerogenes* |
| IX | Mouth | Heavy *Klebsiella pneumoniae* and *Candida tropicalis* |
| | Throat | Heavy *Klebsiella pneumoniae* and *Candida tropicalis* |
| | Tongue | Heavy *Klebsiella pneumoniae* and *Candida tropicalis* |
| | Sputum | $10^8$ *Klebsiella pneumoniae*, $10^7$ *Enterococcus* |
| X | Throat | *Lactobacillus* and *Candida albicans* |
| | Sputum | $10^8$ *Klebsiella pneumoniae*, $10^8$ *Enterobacter cloacae*, $10^5$ *Candida kruseii*, $10^4$ *Candida tropicalis*, $10^5$ *Torulopsis glabrata* |
| XI | Throat | Moderate *Staphylococcus aureus* |
| | Sputum | $1 \times 10^7$ *Staphylococcus aureus* |
| XII | Throat | Heavy *Klebsiella pneumoniae* and *Enterobacter aerogenes*, *Candida albicans* |
| | Sputum | $10^8$ *Enterobacter aerogenes* and $10^5$ *Candida albicans* |
| | Blood autopsy | *Enterobacter aerogenes* and *Pseudomonas* |
| XIII | Throat | Normal Flora |
| | Sputum | $10^4$ *Candida tropicalis*, $10^4$ *Torulopsis glabrata* |

*quantitative sputum analysis

As can be seen from Table 3, in some cases the throat has the same organisms at the sputum which means that the patient was either colonized or there was perhaps oral contamination in the sputum sample. Repeat cultures and observations on changing counts would possibly enable the physician to differentiate between these two latter possibilities. If colonization is observed, precautions could then be taken to prevent the establishment of a lung infection. Furthermore, in many instances, the quantitative sputum analysis reveals heavy infection wherein the throat analysis of the throat specimen does not. In this latter case, the data would support the conclusion that there is minimal nasopharyngeal contamination and that a lung infection in this case is highly probable.

EXAMPLE III

This Example is presented to show the mucolytic action (ability to degrade viscosity) of saponin on a clinical sputum specimen. The sputum specimen was 2 milliliters of a grade 2 sputum as defined in Example II above. To measure the viscosity of the sample, a small viscometer was built such as described in "A Simple Method of Measuring Sputum Viscosity", A. O. Jenssen, Scand. J. Resp. Dis.; 54, 290–296 (1973). This viscometer comprises a single plastic block, the bottom face of which was ground plane. In this bottom face, a canal, semicircular in section, was drilled out, ending in a vertical bore adapted to top to a Y fitting, one branch being connected via plastic hose to an air flow regulator, and the other branch of the Y fitting was connected to a water nonometer via plastic tube. An air escape port was drilled into the vertical bore just above the canal. Changes in pressure were measured as a decrease in the height of the water column in the nonometer. The time required to void the viscometer was recorded in seconds. To measure the viscosity of a given sample, the sputum was placed on a glass plate. The viscometer, with constant air flow, was placed on the sputum filling the channel of the viscometer. An air escape port on the side of the viscometer was closed. The time required to empty the viscometer and the maximum deflection of the height of the water column were recorded. The change in height in milliliters of the water column was converted to millilmeters of mercury (pressure) by multiplication by 0.00881. Next, according to the Jenssen article, pressure x seconds x K = viscosity, where K is a calibration constant for the viscometer. The viscometer was calibrated against an Oswald viscometer using glycerol as a primary standard. For this viscometer, K = $13.5 \times 10^3$. The viscosities obtained with grade 2 sputum with and without addition of the purified saponin described in Example I and II are shown in Table 4 below:

Table 4

| Mucolytic Action of Saponin on a Clinical Sputum Specimen | |
|---|---|
| Nature of sputum: 2 ml of a grade 2.0 sputum. | |
| | Centipoise |
| A. Viscosity of 5 different portions before addition of saponin: | 881 |
| | 1,332 |
| | 14,295 |
| | 19,929 |
| | 6,962 |
| | $\overline{X}$ = 8678 |
| | s.d. = 8306 |
| B. Viscosity of 4 different portions after the addition of 0.1 ml of 13% saponin: | 166 |
| | 177 |
| | 161 |
| | 172 |
| | $\overline{X}$ = 169 |
| | s.d. = 7 |

As can be seen, the action of the saponin effectively digested the sputum and resulted in a substantially uniform viscosity of all portions.

While the invention has been described in relation to its preferred embodiments, it is to be understood that various modifications thereof will now be apparent to one of ordinary skill in the art upon reading this specification and it is intended to cover such modifications as fall within the scope of the appended claims.

I claim:

1. In a method of detecting the presence of pathogenic organisms in the respiratory tract wherein a sample of lung fluid is obtained and thereafter analyzed for the presence of microbial pathogens, the improvement comprising:

admixing said sample of lung fluid with an effective mucolytic amount to degrade the viscosity of said lung fluid sample and to impart a substantially uniform viscosity to said sample of lung fluid of a nontoxic saponin which has had microbial toxins removed therefrom which exhibit an apparent molecular weight of less than about 600 in an aqueous solution and thereafter thoroughly admixing the resulting sample having said substantially uniform viscosity to uniformly disperse said microbial pathogens therewithin prior to the time that said sample is analyzed.

2. The improved method of claim 1 wherein said nontoxic saponin is admixed with said sample of lung fluid in an amount ranging from about 0.1 to about 20% by weight of said mixtures of lung fluid and saponin.

3. The improved method of claim 1 wherein said nontoxic saponin is admixed with said sample of lung fluid in an amount ranging from about 5 to about 10% by weight of said mixture of lung fluid and saponin.

4. The improved method of claim 2 wherein said nontoxic saponin is contained within an aqueous solution.

5. The improved method of claim 4 wherein said aqueous solution of nontoxic saponin further comprises a minor effective amount of an antifoaming agent which is nontoxic to microbial pathogens.

6. The improved method of claim 5 wherein said sample is analyzed by plating portions of said samples after treatment with said saponin on growth media.

7. In a method of detecting the presence of pathogenic organisms in the respiratory tract wherein a sputum sample is obtained and thereafter analyzed for the presence of microbial pathogens, the improvement comprising:
admixing said sputum sample with an effective mucolytic amount to degrade the viscosity of said sputum sample of a nontoxic saponin which has had microbial toxins removed therefrom which exhibit an apparent molecular weight of less than about 600 in an aqueous solution and allowing the viscosity of said sputum sample to degrade prior to the time that said sample is analyzed.

8. The improved method of claim 7 wherein said nontoxic saponin is admixed with said sputum sample in an amount ranging from about 0.1 to about 20% by weight of said mixture of sputum and saponin.

9. The improved method of claim 1 wherein said nontoxic saponin is admixed with said sputum sample in an amount ranging from about 5 to about 10% by weight of said mixture of sputum and saponin.

10. The improved method of claim 7 wherein said nontoxic saponin is contained within an aqueous solution.

11. The improved method of claim 10 wherein said aqueous solution of nontoxic saponin further comprises a minor effective amount of an antifoaming agent which is nontoxic to microbial pathogens.

12. The improved method of claim 11 wherein said sample is analyzed by plating portions of said samples after treatment with said saponin on growth media.

* * * * *

UNITED STATES PATENT AND TRADEMARK OFFICE
CERTIFICATE OF CORRECTION

PATENT NO. : 4,053,363
DATED : October 11, 1977
INVENTOR(S) : Gordon L. Dorn

It is certified that error appears in the above–identified patent and that said Letters Patent are hereby corrected as shown below:

Abstract, line 1, change "in vitro" to --$\underline{\text{in vitro}}$--.

Col. 5, line 2, change "no" to --not--.

Cols. 5 & 6, Table 1, line 19, change
 "$\underline{\text{Staphylcoccus}}$ VIII 1    ++   +++   ---   +-   ---  ---  ---" to
--$\underline{\text{Staphylcoccus}}$ VIII       1    ++   +++   ---   ++-  ---  ---  ---  --.

Col. 6, lines 63 & 64, change "SDA+λAGENT" to --SDA+AGENT--.

Cols. 9 & 10, line 24, Table 2, (Case No. 30), delete
 "(H)     $1 \times 10^8$ $\underline{\text{Haemo-}}$      and $\underline{\text{Haemophilus}}$";

line 46, Table 2, (Case No. 39), delete "albi";

line 50, Table 2, (Case No. 40), change
 "$\underline{\text{Klebsiella pneumonidae}}$" to --$\underline{\text{Klebsiella pneumoniae}}$, and change "$\underline{\text{Canadida albicans}}$" to --$\underline{\text{Candida albicans}}$--;

lines 57-62, Table 2, (Case No. 44) change
"44   4   heavy $\underline{\text{Can-}}$       Positive for    $<10^6$ $\underline{\text{Candida albi-}}$   Positive for
         $\underline{\text{dida albi-}}$     $\underline{\text{Candida abli-}}$     cans, $10^5$ $\underline{\text{Ser-}}$      $\underline{\text{Candida albi-}}$
         $\underline{\text{cans}}$                                  possi                     $\underline{\text{cans, liquefa-}}$
         ratia         ble positive
         liquefa-      for
                                       ciens, $10^5$ Pseudo     Serratia
                                       monas                    liquefaciens
                                                                and Pseudo-
                                                                monas

UNITED STATES PATENT AND TRADEMARK OFFICE
CERTIFICATE OF CORRECTION

PATENT NO. : 4,053,363
DATED : October 11, 1977
INVENTOR(S) : Gordon L. Dorn

It is certified that error appears in the above-identified patent and that said Letters Patent are hereby corrected as shown below:

to
--44  4  Heavy <u>Candida albicans</u>  Positive for <u>Candida albicans</u>  $<10^6$ <u>Candida albicans</u>, $10^5$ <u>Serratia liquefaciens</u>, $10^5$ <u>Pseudomonas</u>  Positive for <u>Candida albicans</u>, possible positive for <u>Serratia liquefaciens</u> and <u>Pseudomonas</u>

Col. 13, line 48, change "Scand. J. Resp. Dis." to --<u>Scand. J. Resp. Dis.</u>--

Signed and Sealed this

First Day of August 1978

[SEAL]

Attest:

RUTH C. MASON
*Attesting Officer*

DONALD W. BANNER
*Commissioner of Patents and Trademarks*